US011246525B2

(12) United States Patent
Vayatis et al.

(10) Patent No.: US 11,246,525 B2
(45) Date of Patent: Feb. 15, 2022

(54) METHOD FOR QUANTIFYING BALANCE

(71) Applicants: ASSISTANCE PUBLIQUE-HOPITAUX DE PARIS, Paris (FR); CENTRE NATIONAL DE LA RECHERCHE SCIENTIFIQUE, Paris (FR); ETAT FRANCAIS—MINISTERE DE LA DEFENSE—DIRECTION CENTRALE DU SERVICE DE SANTE DES ARMEES, Paris (FR); ÉCOLE NORMALE SUPERIEURE PARIS-SACLAY, Cachan (FR); UNIV PARIS XIII PARIS-NORD VILLETANEUSE, Villetaneuse (FR); UNIVERSITE DE PARIS, Paris (FR)

(72) Inventors: Nicolas Vayatis, Paris (FR); Pierre Paul Vidal, Paris (FR); Julien Audiffren, Fribourg (CH); Alain Yelnik, Malakoff (FR); Damien Ricard, Clamart (FR); Ioannis Bargiotas, Paris (FR); Laurent Oudre, Paris (FR); Stéphane Buffat, Paris (FR)

(73) Assignees: ASSISTANCE PUBLIQUE-HOPITAUX DE PARIS, Paris (FR); CENTRE NATIONAL DE LA RECHERCHE SCIENTIFIQUE, Paris (FR); ETAT FRANCAIS—MINISTERE DE LA DEFENSE—DIRECTION CENTRALE DU SERVICE DE SANTE DES ARMEES, Paris (FR); ECOLE NORMALE SUPERIEURE PARIS-SACLAY, Cachan (FR); UNIV PARIS XIII PARIS-NORD VILLETANEUSE, Villetaneuse (FR); UNIVERSITE DE PARIS, Paris (FR)

( * ) Notice: Subject to any disclaimer, the term of this patent is extended or adjusted under 35 U.S.C. 154(b) by 0 days.

(21) Appl. No.: 16/763,573

(22) PCT Filed: Nov. 16, 2018

(86) PCT No.: PCT/FR2018/052895
§ 371 (c)(1),
(2) Date: May 13, 2020

(87) PCT Pub. No.: WO2019/097188
PCT Pub. Date: May 23, 2019

(65) Prior Publication Data
US 2020/0375520 A1 Dec. 3, 2020

(30) Foreign Application Priority Data

Nov. 17, 2017 (FR) .................................... 1760888

(51) Int. Cl.
*A61B 5/11* (2006.01)
*A61B 5/00* (2006.01)
(Continued)

(52) U.S. Cl.
CPC .......... *A61B 5/4023* (2013.01); *A61B 5/1122* (2013.01); *A61B 5/7264* (2013.01);
(Continued)

(58) Field of Classification Search
CPC ... A61B 5/4023; A61B 5/1122; A61B 5/7264; A61B 2562/0247; G06N 7/005; G06N 20/00
See application file for complete search history.

(56) References Cited

U.S. PATENT DOCUMENTS

| | | | |
|---|---|---|---|
| 5,388,591 A | 2/1995 | De Luca et al. | |
| 2012/0253233 A1* | 10/2012 | Greene | G16H 50/30 600/592 |

(Continued)

OTHER PUBLICATIONS

Quagliarella et al, "Influence of the Test Duration in Posturography Performed by Healthy Adults, THA and TKA Patients", pp. 1-4 (Year: 2011).*

(Continued)

*Primary Examiner* — Eyob Hagos
(74) *Attorney, Agent, or Firm* — Pearne & Gordon LLP

(57) ABSTRACT

A method for quantifying the balance of an individual includes segmenting, as a function of time, a statokinesigram(s) of an individual so as to generate several statokinesigram portions; extracting, from the statokinesigram portions, values of at least one trajectory parameter; determining the value of at least two quantifiers, from the values of trajectory parameters extracted in the extraction step, for each of the statokinesigram portions generated in the segmentation step; and determining said value representative of the balance of the individual from the values of the quantifiers of each of the statokinesigram portions. The method may be implemented by a processor and memory.

17 Claims, 5 Drawing Sheets

Figure 1:
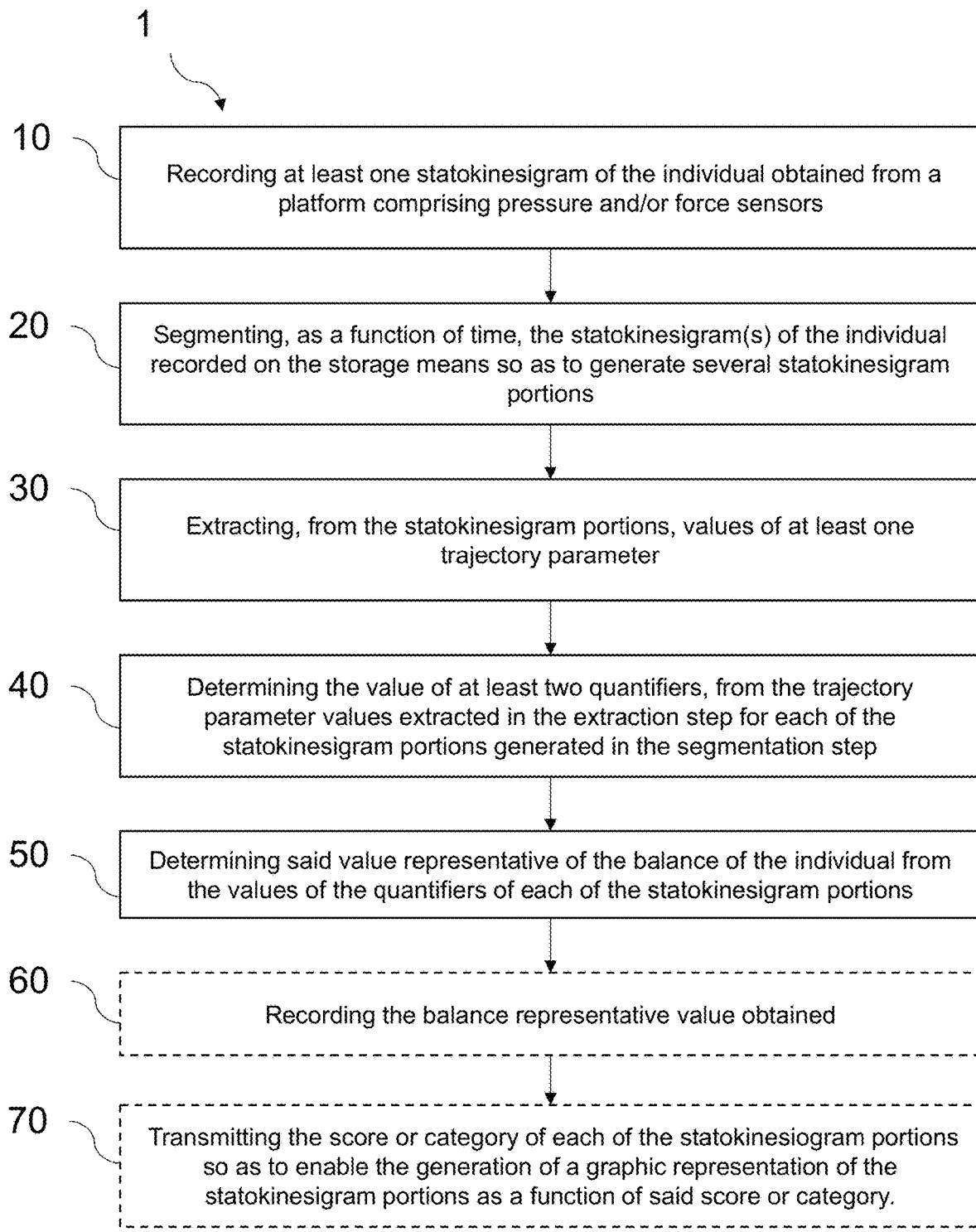

(51) Int. Cl.
*G06N 20/00* (2019.01)
*G06N 7/00* (2006.01)

(52) U.S. Cl.
CPC ............. *G06N 7/005* (2013.01); *G06N 20/00* (2019.01); *A61B 2562/0247* (2013.01)

(56) References Cited

U.S. PATENT DOCUMENTS

| 2014/0081177 A1* | 3/2014 | Eguibar | A61B 5/1036 600/595 |
| 2014/0180172 A1* | 6/2014 | Uchiyama | A61B 5/1116 600/595 |
| 2015/0282766 A1* | 10/2015 | Cole | A61B 5/1038 702/139 |
| 2016/0007902 A1* | 1/2016 | Hewson | G01G 23/3742 600/592 |
| 2017/0000387 A1* | 1/2017 | Forth | G06N 7/005 |

OTHER PUBLICATIONS

Melzer et al., "Postural stability in the elderly: a comparison between fallers and non-fallers". pp. 602-606 (Year: 2004).*
Aguila et al., "Visual Data Exploration for Balance Quantification in Real-Time During Exergaming", pp. 1-22 (Year: 2017).*
Yu et al., "An Online One Class Support Vector Machine-Based Person-Specific Fall Detection System for Monitoring an Elderly Individual in a Room Environment", pp. 1002-1013 (Year: 2013).*
Gagey et al. "Manual Therapy, Posturology and Rehabilitation Journal", pp. 1-3 (Year: 2016).*
Audiffren, et al. "A Non Linear Scoring Approach for Evaluating Balance: Classification of Elderly as Fallers and Non-Fallers." PLOS ONE., vol. 11, No. 12 Dec. 9, 2016. 12 pages.
Written Opinion issued in PCT/FR2018/052895 dated Feb. 28, 2019 (with translation), 12 pages.
International Search Report issued in PCT/FR2018/052895 dated Feb. 28, 2019 (with translation), 7 pages.

* cited by examiner

METHOD FOR QUANTIFYING BALANCE

The present invention relates to the field of the quantification of the balance of an individual. More particularly, the present invention relates to a method for quantifying the balance of a person, a device able to implement this method and a system integrating said device. The present invention allows in particular to monitor the evolution of this balance in particular in order to warn of risks of falling, for example within the framework of a rehabilitation process, in a self-quantification approach or in the elderly.

PRIOR ART

Static and dynamic balances are essential components of our daily movements and a lack of balance is a major cause of falls. Postural control is achieved through the combination of visual, proprioceptive and vestibular systems, as well as of the central nervous system. Deficiencies or disorders of these systems can progressively deteriorate the individual's postural control and therefore increase the risk of falling.

According to estimates of the World Health Organization in 2012, nearly 424,000 people worldwide lose their lives each year due to falls, thus placing falls in the second place of accidental death causes in the world. According to the Institut de Veille Sanitaire, there are 450,000 falls each year in France among people over 65 years and it is the most frequent cause of death among the elderly with 4000 to 4500 cases per year in France.

People falling is therefore a major public health problem because of its frequency and its medical and social consequences; especially and particularly among the elderly. Indeed, falls are now considered one of the leading causes of injury in the elderly and, if they do not result in death, they can lead to a further reduction in mobility and/or autonomy in daily activities. For example, post-fall syndrome results in a phobia of falling with a loss of self-confidence to perform everyday acts and ultimately leads to grabatization.

Consequently, accurate risk assessment has become an important issue, given that one third of the elderly population (namely age over 65) faces at least one fall per year. Despite these challenges, there is currently no intuitive, reliable, and inexpensive method or device for quantifying the balance of an individual. Physicians nowadays appreciate balance through methods for visually monitoring the patient, for example through standardized tests such as the Romberg test. The latter can help the physician make a diagnosis and identify the possible causes of a static ataxia. Nevertheless, such monitoring allows to qualify and not to objectively quantify the balance of an individual. However, quantitative methods could allow to strengthen the sensitivity, objectivity and homogeneity of the interpretations, and would give the possibility of making comparisons of such tests (for example monitoring over time or within a group of individuals) or to identify imperceptible behaviors via methods for visually monitoring the patient.

In this context, the use of force platforms to quantify and evaluate postural control is becoming more widespread. Such platforms record the displacement of the center of pressure ("center of pressure"—COP, in Anglo-Saxon terminology) that is applied by the whole body over time while the individual is standing on the platform. This measurement is used to generate a statokinesigram. Empirical indices derived from the displacement of the COP have been proposed previously such as the length of the displacement of the COP or the variance of the displacement speed of the COP. These indices have shown that statokinesigrams can be significantly affected by the postural control of individuals. As discussed in document U.S. Pat. No. 5,388,591, the statokinesigram may subsequently undergo temporal processing of its data in order to generate a scatter plot of the statokinesigram highlighting the indices to evaluate a subject's postural stability. In addition, it was proposed that the energy distribution of specific frequency bands could inform the chosen postural strategies. Consistent with the above, previous analyses have applied to statokinesigrams a short-term Fourier-transform (STFT—"short-term Fourier transform" in Anglo-Saxon terminology) type analysis or a time-scale wavelet analysis ("time-scale wavelet analysis" in Anglo-Saxon terminology) in order to evaluate the transitions between postural strategies. STFT allows to analyze the temporal changes in the spectral content of the COP displacement (Schumann et al., 1995. Time-frequency analysis of postural sway. J. Biomechanics, Vol. 28, No. 5, pages 603-607). Work on time-scale wavelet analysis has shown that there is a link between frequency bands and the main sensory inputs: the low frequency band (<0.1 Hz) is associated with visual control, frequencies between 0.1 and 0.5 Hz are dominated by vestibular activity, while the 0.5-1 Hz frequency band reflects somatosensory activity. Studies based on this type of analysis have concluded, among other things, that for the evaluation of posturographic data, it is preferable to conduct tests of at least 60 s, otherwise misinterpretations may occur due to misestimates or even biased extracts of an overall process (Kirchner et al. 2012, Evaluation of the temporal structure of postural sway fluctuations based on a comprehensive set of analysis tools. Physica A 391 (2012) 4692-4703). Moreover, the only information obtained when implementing these methods is the frequency band energy distribution and the user is no longer able to assess well-established parameters such as the amplitude of the displacements along the antero-posterior and medio-lateral axes or the displacement surface. Recent work has used the combination of parameters, in multiparameter analyses of statokinesigrams, to identify patients at risk of falling compared to non-fallers (Audiffren et al., 2016, A nonlinear scoring approach for evaluating balance: classification of elderly as fallers and non-fallers. PLoS ONE 11 (12)). Where quantification methods have been used, they have not been able to produce sufficiently satisfactory results because the data to be studied are very complex and difficult to model. Several reasons hinder its use: cost of acquisition, of performance, reproducibility of examinations, sensitivity, specificity, and difficulties in interpreting the results.

Thus, the analytical methods previously used to evaluate the balance do not provide a unique and reliable value that can be easily measured using a simple and inexpensive device. There is therefore a need for a device for balance quantification that can be used by anyone who wants to monitor one's balance and at a low cost, but also by public authorities or health personnel.

Technical Problem

The invention aims to overcome the disadvantages of the prior art. In particular, the invention aims to provide a reliable method for quantifying the balance, that is to say for establishing a value representative of the balance state of the individual, that is rapid, simple, and does not necessarily require the intervention of a specialist in the posturology field. It should be noted that this method is not intended to replace the general practitioner or specialist and does not make a diagnosis. In addition, the method must be able to identify weak signals contained in the statokinesigrams in order to increase its reliability.

The invention also aims to provide a balance quantification device that can be integrated into a complete balance quantification system.

BRIEF DESCRIPTION OF THE INVENTION

To this end, the invention relates to a method for quantifying the balance of an individual to obtain a value representative of the balance of said individual, said method being implemented by a device comprising at least one data processing module connected to a storage means, said method comprising recording (10), on the storage means (280), at least one statokinesigram (110) of the individual obtained from a platform (310) comprising pressure and/or force sensors (312), said method being characterized in that it further comprises the following steps:

segmenting as a function of time, the statokinesigram(s) of the individual recorded on the storage means, by the data processing module, so as to generate several statokinesigram portions, extracting, by the data processing module and from the statokinesigram portions, values of at least one trajectory parameter, said trajectory parameter preferably being a position, stability, and/or dynamics trajectory parameter, determining, by the data processing module, the value of at least two quantifiers, from the values of trajectory parameters extracted in the extraction step for each of the statokinesigram portions generated in the segmentation step, determining, by the data processing module, said value representative of the balance of the individual from the values of the quantifiers of each of the statokinesigram portions.

Statokinesigrams can have varying displacement dynamics of the center of pressure during recording thereof. Previous approaches, for example multidimensional approaches, have attempted to characterize statokinesigrams comprehensively. In particular, such an approach is based on the implicit assumption that the signal may have a uniform profile. Consequently, although the latter methods have been of major use, they have the disadvantage of being sensitive to non-uniformity of statokinesigrams and the existence of short periods of time associated with transient postural imbalance. These transient imbalances may go unnoticed in a global analysis of statokinesigrams, as their durations are usually several tens of seconds.

Segmentation allows each portion to be analyzed independently of the other statokinesigram portions in order to identify weak signals of balance deficit in an individual. Indeed, an episode of disturbance of balance lasting a few seconds could be enough for a person to fall but may not be identified when analyzing a statokinesigram of several tens of seconds taken in its entirety. The implementation of this method includes determining several quantifiers for a same portion which are then jointly processed in a step of determining a value representative of the balance.

According to other optional features of the method:
the statokinesigram portions have a duration of three seconds or less. Indeed, the inventors determined that when the statokinesigram is segmented into portions of three seconds or less, then the reliability of the method is improved;

the segmentation step generates, for each statokinesigram, at least ten statokinesigram portions. A plurality of portions studied in the step of determining the representative value of the balance improves the reliability of the method;

the statokinesigram portions generated in the segmentation step have, for consecutive portions, an overlap ratio of at least 25%, preferably at least 50%. As will be shown in the examples and although this may increase the processing and determination time, the inventors determined that when the portions have an overlap, then the reliability of the method is improved;

the statokinesigram portions generated in the segmentation step have, for consecutive portions, an overlap ratio of at most 95%.

the determination step is carried out by implementing the values of the quantifiers determined in the determination step in a scoring algorithm so as to, depending on the values of the quantifiers, assign a score to each of the statokinesiogram portions or classify each of the statokinesiogram portions by categories. The score may be, for example, a representative score of a characteristic of the displacement of the center of pressure (regular or irregular) or it may be representative of the quality of the individual's balance on each portion of the statokinesigram. Alternatively, the method may allow each portion to be associated with a category such as "good balance" or "balance at risk";

it further comprises a step of transmitting, on a viewing means, the score or category of each of the statokinesiogram portions so as to enable the generation of a graphic representation of the statokinesigram portions as a function of said score or category. Such a step allows a user to directly identify the portions of statokinesigrams that may present an episode of postural imbalance or an episode characteristic of a risk of balance disorder. Beyond an overall score, the user can then treat each of the portions individually in order to improve the quantification and qualification of the balance;

the scoring algorithm is an unsupervised partitioning algorithm. Thus, the method can be implemented without the need for a database;

the unsupervised partitioning algorithm is selected from an unsupervised Gaussian mixture model, a hierarchical bottom-up classification, a hierarchical top-down classification. It is advantageously an unsupervised Gaussian mixture model;

the scoring algorithm is previously calibrated on the basis of the values of the same quantifiers obtained from reference statokinesigram portions. It is then preferably a supervised learning algorithm;

it further comprises a step of generating raw data corresponding to the displacement of the center of a pressure applied by the whole body of an individual over time on a platform. It corresponds to the displacement of the center of pressure;

it further comprises a step of transforming the raw data into trajectory data of the center of pressure;

the raw data corresponding to the displacement of the center of pressure of an individual is obtained in a Romberg test;

the segmentation step is performed from a statokinesigram obtained while the individual has his/her eyes open and a statokinesigram obtained while the individual has his/her eyes closed;

it includes, for at least one quantifier, calculating an O/F or F/O ratio corresponding to the ratio between the value of a trajectory parameter calculated from a statokinesigram obtained while the individual has his/her eyes open and the value of a trajectory parameter calculated from a statokinesigram obtained while the individual has his/her eyes closed (O/F ratio) or the opposite (F/O ratio); and/or an acquisition time of a statokinesigram can be between 5 and 70 seconds;

the trajectory parameter is a position, stability, and/or dynamics trajectory parameter of the center of pressure.

The invention further relates to a device for quantifying the balance of an individual, said device comprising:

a communication module able to receive a statokinesigram of said individual, a storage means able to record said statokinesigram, and at least one data processing module, able to connect to the storage means, characterized in that the data processing module is configured to:

Segment as a function of time the statokinesigram of the individual recorded on the storage means so as to generate several statokinesigram portions, Extract, from the statokinesigram portions, values of at least one trajectory parameter, Determine at least two quantifiers, from the values of the extracted trajectory parameters, Determine a value representative of the balance of the individual from the values of said quantifiers of each of the statokinesigram portions.

According to other optional features of the device:

the communication module is configured to receive and transmit information to remote systems;

it further includes a statokinesigram generation module configured to generate data relating to a statokinesigram; and/or it further includes a re-sampling module configured to process the raw data or the statokinesigrams at a first frequency in order to generate statokinesigrams re-sampled at a second frequency and having a substantially constant frequency.

The invention further relates to a system for quantifying the balance of an individual, comprising:

a platform, said platform being adapted to receive an individual and comprising pressure and/or force sensors configured to generate raw data, at a first frequency, as a function of a pressure exerted by the feet of the individual on the platform, a raw data processing unit, arranged to obtain at least one statokinesigram of the individual from the raw data generated by the platform, and a balance quantification device according to the invention, able to communicate with the processing unit.

According to other optional features of the system:

the platform includes four pressure and/or force sensors.

the platform is configured to measure the values of its different pressure and/or force sensors at a frequency greater than or equal to 25 Hz and substantially constantly.

the platform includes a foam capable of distorting or disrupting proprioceptive and tactile information.

The invention further relates to a product computer program configured to implement the quantification method according to the invention, said computer program including at least:

one algorithm adapted to segment a statokinesigram of an individual so as to generate several statokinesigram portions, one algorithm adapted to extract, from the statokinesigram portions, values of at least one trajectory parameter, one algorithm adapted to determine several quantifiers, from the extracted values of the trajectory parameters, and one algorithm adapted to determine a value representative of the balance of the individual from the values of said quantifiers of each of the statokinesigram portions.

Other advantages and characteristics of the invention will appear upon reading the following description given by way of illustrative and non-limiting example, with reference to the appended figures which represent:

FIG. 1, a diagram of the equilibrium quantification method according to the invention. The steps in dotted boxes are optional.

Figure 2A:
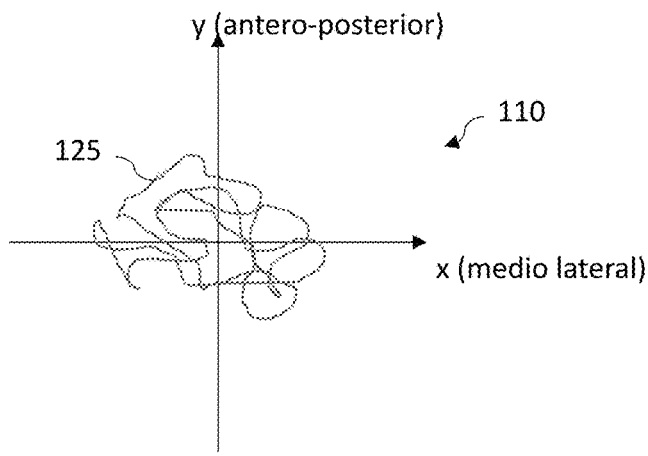
Figure 2B:
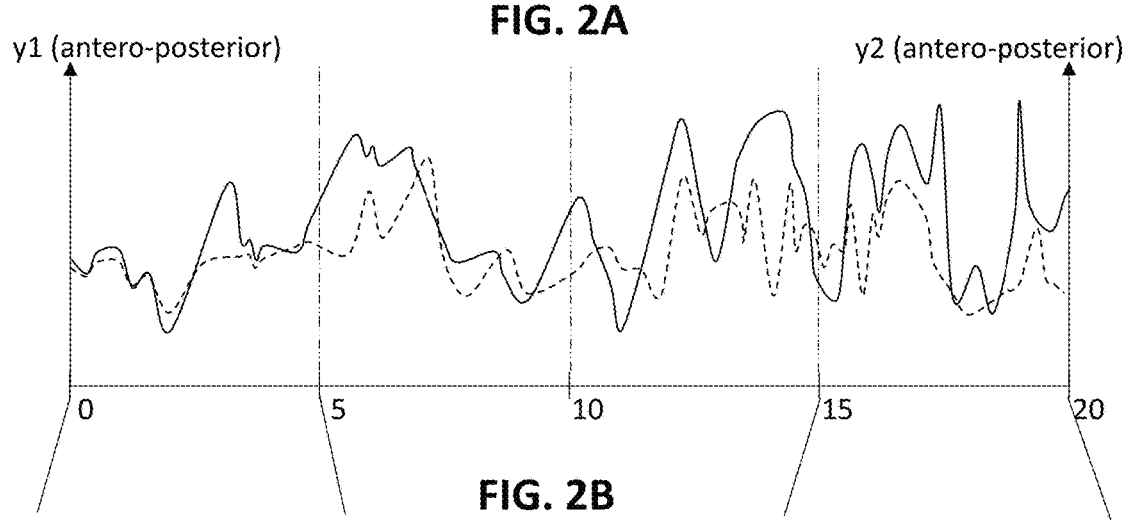
Figure 2C:
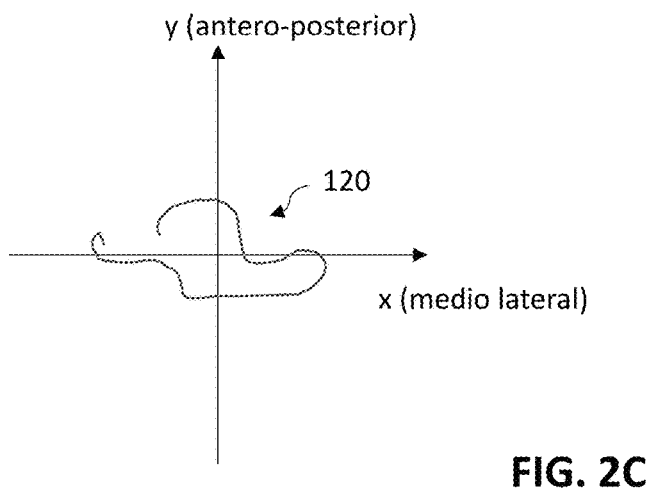
Figure 2C:
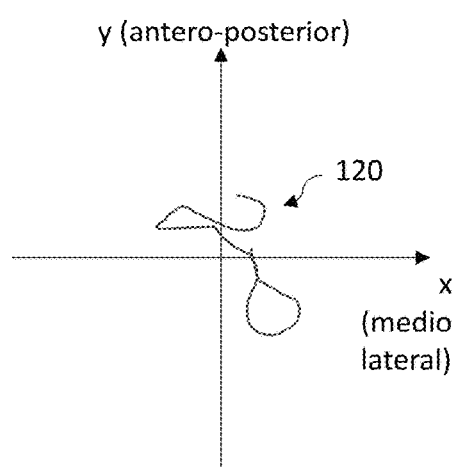
Figure 2D:
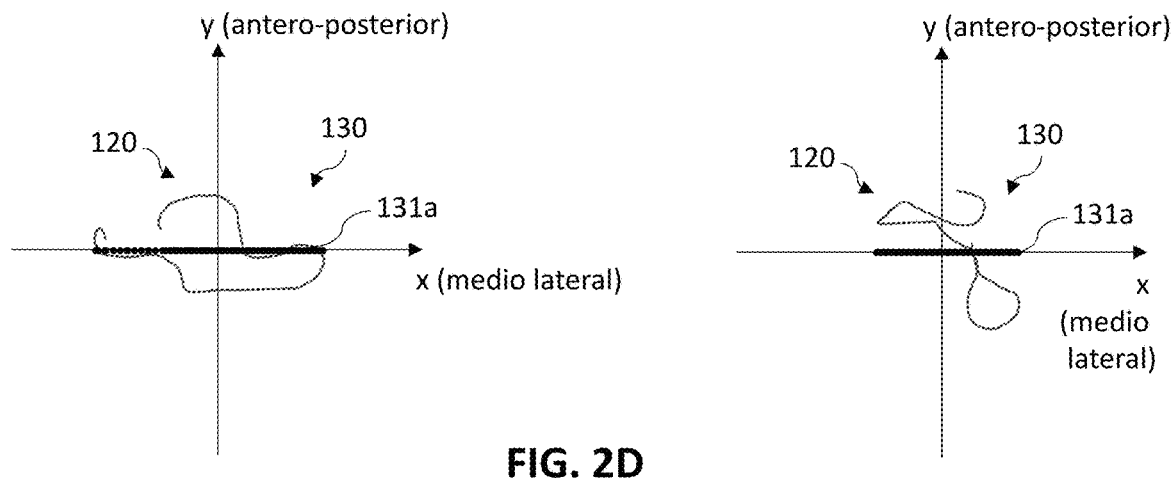
Figure 2E:
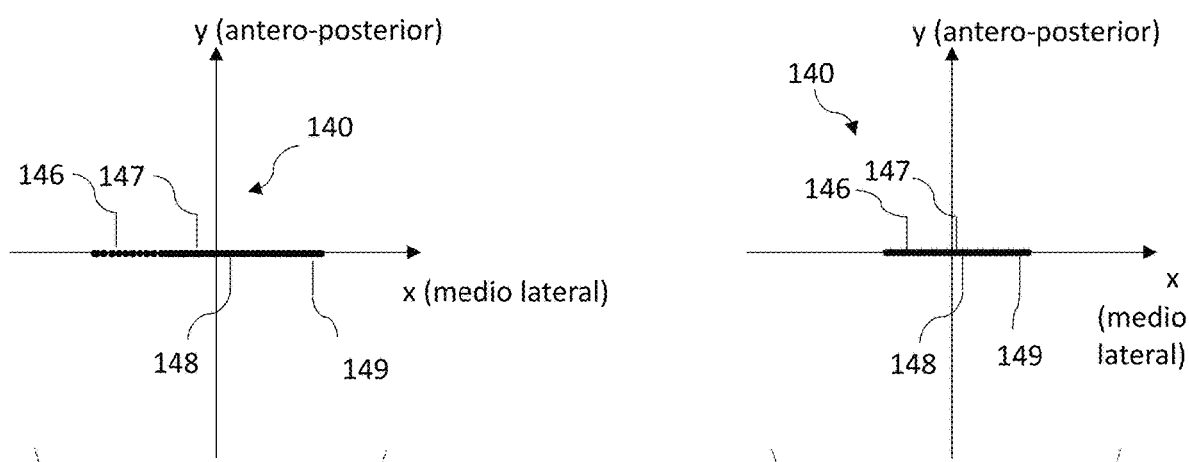
Figure 2F:
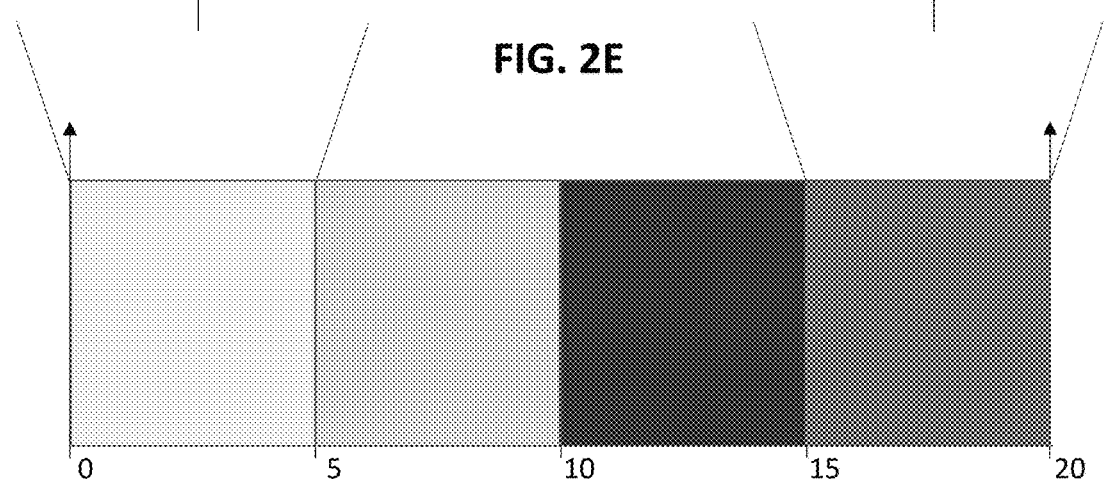

FIG. 2A illustrates a statokinesigram according to the invention where the y-axis corresponds to the antero-posterior axis and the x-axis to the medio-lateral axis. FIG. 2B plotted on a 20-second time axis and segmented into four portions of five seconds each. FIG. 2C illustrates two statokinesigrams showing displacement data associated with the 0-5 second portion and the 15-20 second portion, respectively, of the data segments in FIG. 2B. FIG. 2D shows the projection on the X-axis of a set of values of a parameter disclosed herein from a portion of the statokinesigram shown in FIG. 2A. FIG. 2E shows the projection on the X-axis of all the values of the aforementioned parameter, as well as other information as herein disclosed. FIG. 2F is a graphical representation of the portions of the statokinesigram as a function of the score of each portion.

Figure 3:
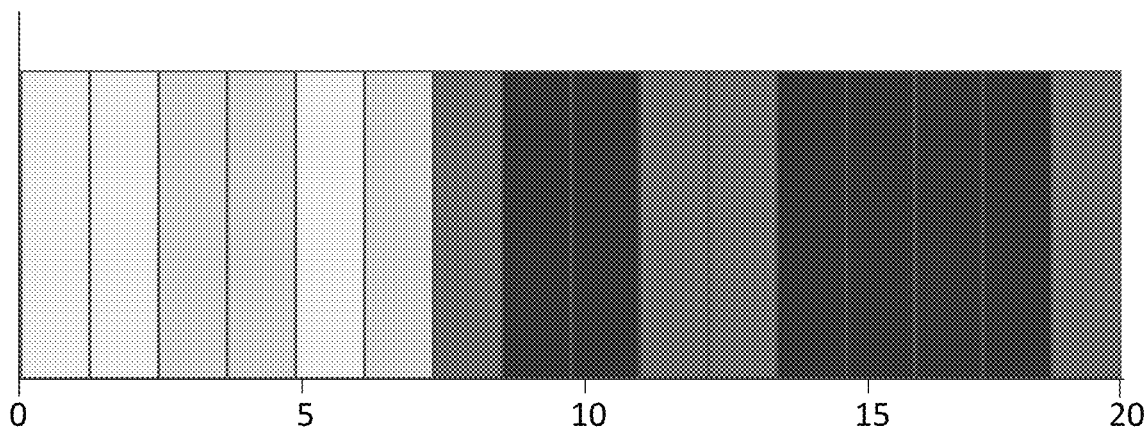

FIG. 3, an illustration of a graphical representation over time of the portions of the statokinesigram as a function of the score of each portion.

Figure 4:
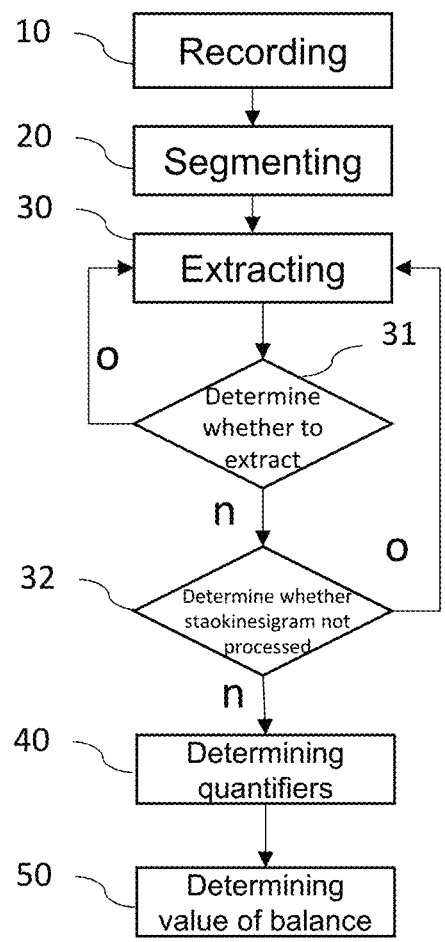

FIG. 4, a schematic diagram of an implementation of the method according to the invention.

Figure 5:
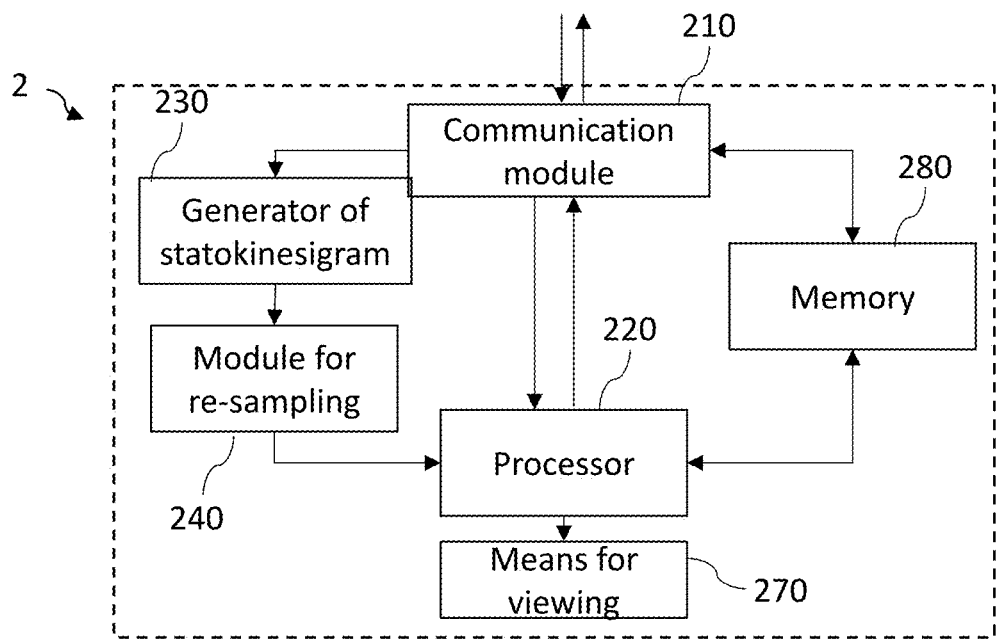

FIG. 5, a balance quantification device according to the invention.

Figure 6:
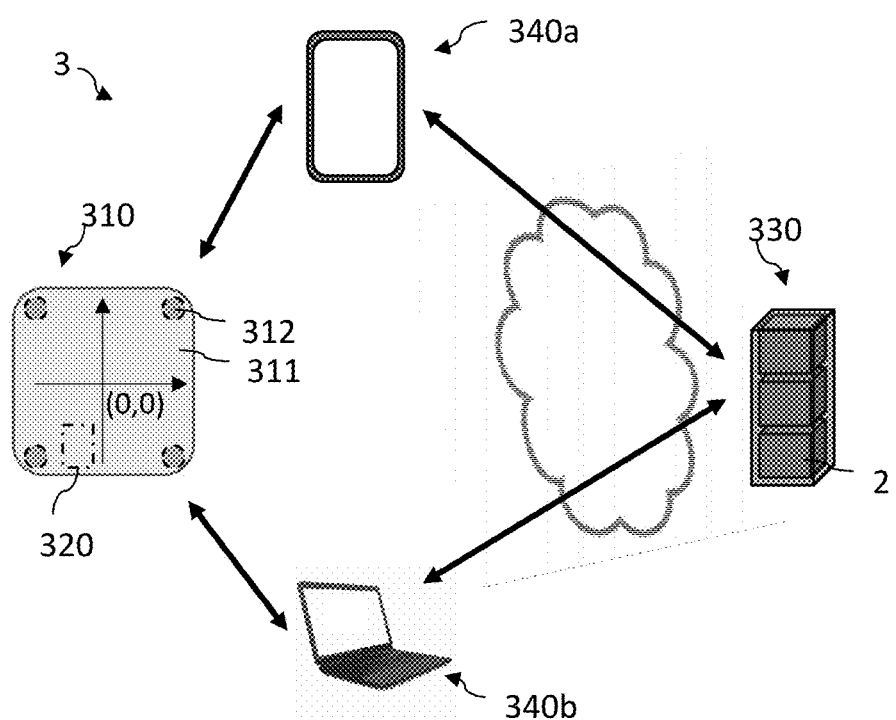

FIG. 6, a balance quantification system according to the invention.

DESCRIPTION OF THE INVENTION

In the following description, the "balance", within the meaning of the invention, corresponds to the postural balance linked to the stability of the body and more particularly to the stability the center of gravity of an individual. The notion of balance according to the invention is linked to the ability of an individual to avoid falling and encompasses static balance and dynamic balance.

The "balance quantification" corresponds, within the meaning of the invention, to the assignment of a value, for example a score, a classification, or a grade, to a trajectory or to a displacement of the center of pressure of an individual. This balance quantification allows to obtain a value representative of the balance and can be performed based on many linear or non-linear scales of different sizes (for example 1, 5, 10, 100). The balance representative value assigned when quantifying the balance can also allow to assign an individual to a group, for example via a decision rule. The quantification according to the invention can be performed, in particular, by implementing a scoring algorithm generated from a partitioning or learning statistical method.

By "model" or "rule" or "scoring algorithm" must be understood, within the meaning of the invention, a finite series of operations or instructions for quantifying the balance, that is to say to classify one or more individuals within previously defined groups Y, to assign a score, or to rank one or more individuals within a classification. Implementing this finite sequence of operations allows, for example, to assign a label $Y_0$ to an observation described by a set of characteristics $X_0$ using, for example, the implementation of a function f likely to reproduce Y, having observed X.

$$Y=f(X)+e$$

where e symbolizes the noise or measurement error

By "supervised learning method" is meant, within the meaning of the invention, a method for defining a function f from a base of n labeled observations $(X_{1\ldots n}, Y_{1\ldots n})$ where $Y=f(X)+e$. By "unsupervised partitioning method", an unsupervised learning method for dividing a dataset into different homogeneous groups, where the homogeneous groups share common characteristics.

Within the meaning of the invention, by "center of gravity" is meant, the center of gravity of the body of an individual. It corresponds, within the meaning of the invention, to the barycenter of the masses of the individual. The center of gravity cannot be maintained in perfect stability and, for example, when standing upright, the center of gravity oscillates from front to back and from left to right.

Within the meaning of the invention, by "center of pressure" is meant, the projection on the horizontal plane passing through the point of contact between the subject and the ground of the barycenter of the vertical forces exerted on the ground by the body of the subject (Benda, B. J. Et al. 1994 Biomechanical relationship between center of gravity and center of pressure during standing. Rehabilitation Engineering, IEEE Transactions on 1994, 2, 3-10). These measurements can be made using a platform analyzing the distribution of the pressures under the foot bed such as a force platform or a shoe or a deformable ground. Without being an exact projection of the center of gravity, the center of pressure is strongly linked to the center of gravity. The displacement of the center of pressure is generally faster and wider than that of the center of gravity in order to keep it in balance. It reflects the efforts made by an individual to control the position of his/her center of gravity.

By "statokinesigram" or "trajectory of the center of pressure", are meant the data related to the trajectory or displacement of the center of pressure. The statokinesigram can also be called a stabilogram and is usually generated via a platform such as a force platform, an "intelligent" floor equipped with sensors or soles equipped with pressure sensors. It corresponds to the calculated trajectory of the center of pressure over time. The trajectory of the center of pressure is defined by a set of position data in an orthonormal reference frame x,y as a function of time and over a defined period of time.

By "segmenting a statokinesigram" is meant segmenting, sampling, or partitioning as a function of time, the set of values of the displacement of the center of pressure forming a statokinesigram into several sets of values, called portions of the statokinesigram.

The "platform", within the meaning of the invention, corresponds to a device resting on the ground including sensors, for example of the force or pressure sensor type, producing an electrical, optical, or magnetic signal proportional to the force applied on said platform by the feet of an individual. The sensors used can be, for example, Wheatstone bridge strain gauges in order to generate the 3 force and moment components Fx, Fy, Fz, Mx, My, and Mz; piezoelectric pressure sensors, piezoresistive pressure sensors, or capacitive pressure sensors. Within the meaning of the invention, the platform is configured to generate "raw data" derived from said sensors.

By "parameter" or "trajectory parameter" and more particularly by "parameter calculated from the trajectory of the center of pressure", is meant, within the meaning of the invention, a transformation of the trajectory of the center of pressure into a set of values.

By "quantifier" and more particularly by "quantifier calculated from a transformation of a trajectory parameter" is meant, within the meaning of the invention, a single value obtained by selecting or transforming all the values of a trajectory parameter.

By "reference quantifier" is meant a value obtained from a reference statokinesigram from a person whose balance was previously qualified.

Within the meaning of the invention, the "ROC (Receiver Operating Characteristic) curve" represents the evolution of the sensitivity (true positive rate) as a function of the specificity (false positive rate) of a model for each given threshold value. It is a curve rising between the point (0,0) and the point (1,1) and it is normally located above the first bisector. Indeed, a random prediction would give a line corresponding to the first bisector. For an ROC curve, the higher the curve above the first bisector, the better the prediction and the area under the ROC curve (AUC—Area Under the Curve in Anglo-Saxon terminology) is indicative of the quality of the model (1 for an ideal prediction, 0.5 for a random prediction).

By "process", "calculate", "determine", "display", "extract", "compare" or more broadly "executable operation" is meant, within the meaning of the invention, an action performed by a device or processor unless the context indicates otherwise. In this respect, operations refer to actions and/or processes in a data processing system, such as a computer system or electronic computing device, which manipulates and transforms data represented as physical (electronic) quantities in the memories of the computer system or other devices for storing, transmitting or displaying information. These operations can be based on applications or software.

The terms or expressions "application", "software", "program code", and "executable code" mean any expression, code or notation, in a set of instructions designed to cause data processing to perform a particular function directly or indirectly (for example after an operation of conversion to another code). Examples of program code may include, but are not limited to, a sub-program, function, executable application, source code, object code, library and/or any other sequence of instructions designed for execution on a computer system.

By "processor" is meant, within the meaning of the invention, at least one hardware circuit configured to perform operations according to instructions contained in a code. The hardware circuit can be an integrated circuit. Examples of a processor include, but are not limited to, a central processing unit, a graphics processor, an application-specific integrated circuit (ASIC) and a programmable logic circuit.

By "coupled" is meant, within the meaning of the invention, connected, directly or indirectly with one or more intermediate elements. Two elements can be coupled mechanically, electrically, or linked by a communication channel.

In the following description, the same references are used to designate the same elements.

According to a first aspect, the invention relates to a method for quantifying the balance of an individual to obtain a value representative of the balance of said individual.

The balance quantification method 1 according to the invention is based on processing the trajectory data of the center of pressure of an individual such as transcribed in a statokinesigram 110. These trajectory data of the center of pressure of an individual are generally acquired when the individual is standing up.

The influence of visual afferents on stability can be measured by generating two displacement or trajectory kinetics of the center of pressure, a first one with the eyes open and a second one with the eyes closed. Thus, preferably, the segmentation step 20 is performed from a statokinesigram 110 obtained while the individual has his/her eyes open and a statokinesigram 110 obtained while the individual has his/her eyes closed. In particular, the acquisition time of a statokinesigram 110 can be between 5 and 70 seconds, preferably between 20 and 60 seconds, and even more preferably between 20 and 40 seconds.

Advantageously, the trajectory data of the center of pressure can be obtained during a Romberg test. The Romberg test consists of placing the individual standing up, motionless, arms along the body, looking straight ahead. The displacement of the center of pressure is recorded for 25 seconds. For example, a 25-second recording is made with the eyes open and another 25-second recording is made with the eyes closed.

The method according to the invention can be implemented from the data related to the displacement of the center of pressure, that is to say based on at least one statokinesigram 110 or based on the raw data derived from the sensors and related to the displacement of the center of pressure.

As shown in FIG. 1, the method according to the invention includes several steps. In addition, some of these steps are illustrated in FIG. 2. The method according to the invention is preferably implemented by a device comprising at least one data processing module 220 connected, or coupled, to a storage means 280.

The method comprises in particular a step of recording 10 at least one statokinesigram 110 of the individual obtained for example from a platform 310 comprising pressure and/or force sensors 312. This recording step is preferably implemented on the storage means 280. This recording can be performed on all types of memory such as transient or non-transient memories. This recording is preferably made on a non-transient memory. Thus, the statokinesigram 110 can be generated well before the method according to the invention is implemented and at a remote location. Alternatively, the statokinesigram 110 can be generated just before the balance quantification method 1 according to the invention is implemented and by a same system. Thus, the quantification method 1 according to the invention may thus include a step of generating the raw data corresponding to the displacement of the center of pressure 11 beforehand. This step is nevertheless optional and can be performed before the quantification method 1 according to the invention by known devices and methods. The raw data corresponding to the displacement of the center of pressure are, for example, the pressure values measured by each of the sensors present on the platform. These raw data can be subject to a step of transforming 12 into trajectory data of the center of pressure (namely a statokinesigram). This transformation step is also optional because it can be performed before the method according to the invention by known methods. In addition, the method may include a step of re-sampling the statokinesigram at a frequency of at least 25 Hz. This re-sampling can for example be carried out before the segmentation step. FIG. 2A is a graphical representation of a statokinesigram 110 according to the invention and more particularly of the plot 125 of the statokinesigram 110.

The method according to the invention also includes a step of segmenting 20, as a function of time, the statokinesigram(s) 110 of the individual recorded on the storage means 280, so as to generate several statokinesigram portions 120. This segmentation step 20 is preferably implemented by the data processing module 220.

The statokinesigram portions 120 can have several durations. Preferably, all portions of a same statokinesigram have the same duration. For example, this duration may be five seconds or less, and preferably it is less than or equal to three seconds, for example two seconds, or more preferably one second.

Advantageously, the statokinesigram portions 120 generated in the segmentation step 20 have, for consecutive portions, an overlap ratio of at least 25%, preferably at least 50%. By overlap ratio should be understood that part of the information contained in a portion n is identical to part of the information contained in a portion n+1 and that another part of the information contained in a portion n is identical to part of the information contained in a portion n−1. Thus, in the case of portions with a duration of two seconds with a 25% overlap ratio, then the information contained between t=1.5 seconds and t=2 seconds of a portion n will be identical to the information contained between t=0 second and t=0.5 seconds of a portion n+1. Advantageously, the overlap ratio between two consecutive statokinesigram portions is at most 95%, more preferably at most 90%, more preferably at most 80%, and even more preferably at most 75%.

Preferably, the segmentation step 20 allows the generation, for each statokinesigram, of at least ten statokinesigram portions 120, more preferably at least twenty, and even more preferably at least thirty statokinesigram portions 120. For example, FIG. 2B shows the data from the statokinesigram in FIG. 2A plotted on a 20-second time axis, with said statokinesigram here being segmented into four portions of five seconds each. The displacement data associated with the 0-5 second and 15-20 second portions are shown in FIG. 2C.

The method according to the invention also includes a step of extracting 30, from the statokinesigram portions 120, values of at least one trajectory parameter 130. This extraction step 30 is preferably implemented by the data processing module 220.

The trajectory parameter 130 is preferably a trajectory parameter for the position, stability, and/or dynamics of the center of pressure. Thus, the extraction step 30, by the data processing module 220 and from the statokinesigram portions 120 of the individual comprises extracting 30 the values of at least one trajectory parameter 130:
  for the position 131 of the center of pressure,
  for the stability 132 of the center of pressure, and/or
  for the dynamics 133 of the center of pressure.

In addition, the analysis of several parameters from different parameter families is particularly advantageous. Thus, the extraction step 30, by the data processing module 220 and from the statokinesigram portions 120 of the individual, comprises extracting 30 the values of at least two trajectory parameters:
  for the position 131 of the center of pressure,
  for the stability 132 of the center of pressure, and/or
  for the dynamics 133 of the center of pressure.

More particularly, the position trajectory parameter 131 of the center of pressure can be selected from:

The position of the center of pressure along the X-axis: this position corresponds to the position of the center of pressure compared to the median line of the orthonormal reference frame in a plan of the X-axis. For example, in the case of a position of the center of pressure shifted towards the left at a time t, the position along the X-axis has, for this time t, a negative value indicating a left hyper-support. This position can be measured, for example, in millimeters. For example, FIG. 2D shows the projection on the X-axis of the set of values of the "position of the center of pressure along the X-axis" parameter 131*a*, obtained from a portion 120 of the statokinesigram 110 shown in FIG. 2A;

The position of the center of pressure along the Y-axis: this position corresponds to the position of the center of pressure with respect to the median line of the orthonormal reference frame in a plane of the Y-axis. For example, in the case of a position shifted backwards at a time t, the position along the Y-axis has, for that time t, a negative value indicating a posterior hyper-support. This position can be measured, for example, in millimeters.

The radius in polar coordinates: this distance corresponds to the distance of the center of pressure from the average position of the center of pressure according to the orthonormal reference plane (0,0). For example, if the center of pressure is shifted by 4 millimeters from the average position of the center of pressure along an axis of 60°, at a time t, the radius in polar coordinates has, for that time t, a value of 4 millimeters. Such a transformation, proposed by the inventors, allows to quantify the overall distance of the center of pressure from a point of origin without limiting to the X and Y coordinates of the center of gravity. The radius in polar coordinates is calculated for all sampling points of the displacement of the center of pressure over the duration of the acquisition.

More particularly, the stability trajectory parameter 132 of the center of pressure can be selected from:

The radial balance: it corresponds to the maximum distance of the center of pressure from its current value at a given time over a predefined duration of t seconds. The duration taken into account for calculating the radial balance can be between 0.05 and 10 seconds, preferably between 0.1 and 2 seconds. The radial balance is calculated for all sampling points of the displacement of the center of pressure over the duration of the acquisition. It is thus a function of time and can be measured, for example, in millimeters.

The time balance: it corresponds to the time required for the center of pressure to move more than r millimeters away from its current position at any given time. The distance r taken into account for calculating the time balance can be between 0.1 and 20 millimeters, preferably between 1 and 10 millimeters. The time balance is calculated for all sampling points of the displacement of the center of pressure over the duration of the acquisition. It is thus a function of time and can be measured, for example, in seconds.

The ballistic interval: it corresponds to the time interval between two balance positions. Preferably, a balance position corresponds to a time when the time balance is greater than 60%, preferably greater than 80%, of the maximum observed in the statokinesigram. The ballistic interval is calculated over the duration of the acquisition and the number of values obtained may vary depending on the acquisitions. It is not a function of time and can be measured, for example, in seconds.

More particularly, the dynamics trajectory parameter 133 of the center of pressure can be selected from:

The velocity of the displacement of the center of pressure: it is calculated for all sampling points of the displacement of the center of pressure over the duration of the acquisition. This parameter is thus a function of time and can be measured, for example, in millimeters per seconds.

The acceleration of the displacement of the center of pressure: it is calculated for all sampling points of the displacement of the center of pressure over the duration of the acquisition. It is thus a function of time and can be measured, for example, in millimeters per seconds squared.

The power: it corresponds to the value of the scalar product of the velocity and acceleration calculated for all sampling points. This parameter represents the energy expended by the individual to change the norm of the velocity of the center of pressure.

The deviation: it corresponds to the norm of the vector product of the velocity and acceleration calculated for all sampling points. This parameter represents the energy expended by the individual to change the direction of the velocity of the center of pressure (namely its displacement, its trajectory, or its movement). In the context of the study of a statokinesigram portion 120, the power and deviation are two parameters that can advantageously replace the length of the displacement of the center of pressure, the variance of the velocity as a function of the Y-axis (VFY) or the LFS (namely ratio of length to surface), providing information according to the prior art on the energy consumption expended by the subject to control his/her posture. In particular, the deviation proposed by the inventors allows to evaluate from a new angle the energy expenditure of the individual and is more relevant in the method according to the invention than the parameters proposed in the prior art (for example VFY, LFS).

The method according to the invention also includes a step of determining 40 the value of at least two quantifiers 140, from the trajectory parameter values 130 extracted in the extraction step 30 for each of the statokinesigram portions 120 generated in the segmentation step 20. This step of determining 40 the value of at least two quantifiers 140 is preferably implemented by the data processing module 220.

In the method developed by the inventors, they focused individually on each of the statokinesigram portions generated during the segmentation step. Thus, from the values of one or more trajectory parameters, they calculated at least two quantifiers for each of the portions. Advantageously, the method comprises, in the determination step 40, determining the value of at least three quantifiers 140, preferably at least five quantifiers. This leads to the generation during the determination step 40 of a plurality of quantifiers associated with statokinesigram portions 120.

There is a plurality of possible quantifiers 140. In this context, the inventors have been interested in many other methods for transforming the trajectory parameters 130 in order to generate, from these sets of values and where necessary in combination with other sets of values, a single value representative of the balance of an individual. Thus, new quantifiers 140 never used in the past were generated.

The step of determining 40 several quantifiers 140 from the trajectory parameters 130 therefore consists more particularly in transforming, for each trajectory parameter 130, all the values into a single value that can be used in the context of a comparison, for example via a statistical model. This transformation into a single value (quantifier) can be repeated for several trajectory parameters 130 or for a same trajectory parameter. For example, FIG. 2E shows the projection on the X-axis of all the values of the "position of the center of pressure along the X-axis" parameter, as well as four quantifiers calculated from this parameter, for each graph.

The most informative quantifiers 140 in the context of the quantification method according to the invention are the mean value, the variance, the square mean, or an extreme value, of an extracted trajectory parameter 130. Thus, preferably, the quantification method 1 according to the invention includes, for at least one parameter, calculating the mean value 147, the median value 148, the variance, the square mean, or at least one extreme value 146, 149, of said trajectory parameter 131, 132, 133.

The extreme values of a parameter are obtained by determining a percentile. A percentile, or centile, can be calculated, for example, by ordering and then sorting all the values of a parameter in 100 subsets with a same number of values. FIG. 2E shows the 10 percentile 146 and the 95 percentile 149 of the "position of the center of pressure along the X-axis" parameter corresponding to the highest value of the position of the center of pressure along the X-axis within the lowest 10% of values and the lowest value of the position of the center of pressure along the X-axis within the highest 5% of values, respectively. Thus, the 10 percentile is the value separating 10% of the lowest values and 90% of the highest values while the 95 percentile is the value separating 95% of the lowest values and 5% of the highest values. Preferably, an extreme value of a trajectory parameter 130 corresponds to a percentile less than or equal to 15 or to a percentile greater than or equal to 85; more preferably, to a percentile less than or equal to 10 or to a percentile greater than or equal to 90 and even more preferably to a percentile less than or equal to 5 or to a percentile greater than or equal to 95. Alternatively, an extreme value of a trajectory parameter 130 may correspond to a percentile greater than or equal to the 5 percentile and less than or equal to the 15 percentile (low extreme values) or to a percentile greater than or equal to the 85 percentile and a percentile less than or equal to the 95 percentile (high extreme values).

In addition, beyond the calculation of a quantifier 140, the inventors showed that the comparison eyes open (O)/eyes closed (F) on some parameters or quantifiers would allow to differentiate performance in terms of balance. Thus, in particular, the quantification method 1 according to the invention includes for at least one quantifier, calculating an O/F or F/O ratio.

FIG. 4 shows a particular embodiment of the first steps of the method according to the invention. The method illustrated begins with the step of recording 10 a statokinesigram 110 of an individual. The statokinesigram 110 is then segmented, for example into 1-second portions with an overlap ratio of 50%.

The method then includes a step of extracting 30 the values of a trajectory parameter 130 from a statokinesigram portion. The method then determines 31 whether to extract values from another trajectory parameter 130. If yes (o in the figure) then the step of extracting 30 the values of a trajectory parameter 130 is repeated on the same statokinesigram portion. If not (n in the figure), the method determines 32 whether there is a statokinesigram portion 120 that has not been processed. If yes (o in the figure) then the step of extracting 30 the values of a trajectory parameter 130 is repeated on a new statokinesigram portion 120. If not (n in the figure), the method proceeds to the step of determining 40 the value of at least two quantifiers 140 from the trajectory parameter values. The method performs these calculations until all necessary quantifiers have been calculated. Then, it initiates the phase of determining the value representative of the balance of said individual.

Thus, the method according to the invention also includes a step of determining 50 said value representative of the balance of the individual from the values of the quantifiers of each of the statokinesigram portions 120. This determination step 50 can be implemented by the data processing module 220. Preferably, the determination step 50 can be preceded by a quantifier normalization step 140.

Advantageously, the determination step 50 is performed by implementing the values of the quantifiers 140 determined in the determination step 40 in a scoring algorithm 500, preferably previously calibrated. The scoring algorithm 500 can be pre-calibrated based on the values of the quantifiers 140 or based on the values of the same quantifiers obtained from reference statokinesigram portions 121.

Preferably, the implementation of the scoring algorithm 500 may involve assigning a score to each of the statokinesigram portions 120 depending on the quantifier values. The score may, for example, be a representative score of a characteristic of the displacement of the center of pressure (regular or irregular) or be representative of the quality of the individual's balance on each portion of the statokinesigram. For example, in FIG. 2F and FIG. 3, the method according to the invention allows to give a score to each of the portions of the statokinesigram which is represented by a darker or lighter shade of gray coloration.

Alternatively, the implementation of the scoring algorithm 500 may involve categorizing each of the statokinesigram portions 120 into categories. For example, the method may allow each portion to be associated with a category such as "good balance" or "balance at risk". The category can be selected from at least two categories, for example from five categories and is preferably selected from two categories.

When assigning a score or classification in a category of a statokinesigram portion 120, the method according to the invention may include taking into account a plurality of quantifier values 140.

As will be shown in the examples, the classification may be unsupervised and allow discrimination between a family of portions that has been the most frequent called the regular periods—RP, while the least common, which will be characterized by less stable dynamics, will be considered as the irregular periods—IP. Thus, it can be considered that the second family will be more important and more frequent in the statokinesigrams of individuals more likely to fall than in the statokinesigrams of individuals with a good balance. Consequently, this difference in proportion can be used to determine a value representative of the balance among individuals.

This scoring algorithm 500 may have been built from different learning models, in particular partitioning, supervised, or unsupervised models.

The scoring algorithm 500 is preferably an unsupervised partitioning algorithm. This unsupervised partitioning algorithm can for example be selected from an unsupervised Gaussian mixture model, a hierarchical bottom-up classification (Hierarchical clustering Agglomerative in Anglo- Saxon terminology), a hierarchical top-down classification (Hierarchical clustering divisive in Anglo-Saxon terminology). Preferably, it is an unsupervised Gaussian mixture model.

Alternatively, this scoring algorithm 500 is based on a supervised statistical learning model configured to minimize a risk of the ordering rule and thus allowing to obtain more efficient prediction rules. In this case, the determination 50 may include a step of comparing by the data processing module 220 said values of at least two quantifiers 140 to predetermined values. For example, the predetermined values can be calculated from reference statokinesigram portions 121 stored in a database. The comparison step can be based on a model, trained on a dataset, and configured to predict the label of a statokinesigram portion or a complete statokinesigram. For example, for calibration purposes, it is possible to use a dataset from a set of individuals representative of a population, characterized by several reference statokinesigram portions 121 and their associated reference parameters and/or quantifiers and by a binary label (label or class), for example in the form of "good balance"/"poor balance". The dataset can also comprise multiple labels. In the context of the present invention, the quantification method 1 may be based on at least twenty-five reference statokinesigram portions 121, preferably at least fifty, and even more preferably at least one hundred. The comparison step can then include using a supervised statistical learning model selected for example from the kernel methods (for example Large Margin Separators—Support Vector Machines SVM, Kernel Ridge Regression) described for example in Burges, 1998 (Data Mining and Knowledge Discovery. A Tutorial on Support Vector Machines for Pattern Recognition), the ensemble methods (for example Bagging, Boosting, decision trees, Random Forest) described, for example, in Brieman, 2001 (Machine Learning. Random Forests), or the neural networks described, for example, in Rosenblatt, 1958 (The perceptron: a probabilistic model for information storage and organization in the brain).

In addition, creating the scoring algorithm 500 may include a "Bagging" step and/or a Boosting step. Bagging and its implementation are described in detail in Galar et al. 2011 (A Review on Ensembles for the Class Imbalance Problem: Bagging-, Boosting-, and Hybrid-Based Approaches). Boosting encompasses a set of algorithms such as: Adaboost, LPBoost, TotalBoost, BrownBoost, xgboost, MadaBoost, LogitBoost. Boosting is a sequential method and each sample is drawn according to the performance of the basic rule on the previous sample. Boosting and its implementation are described in detail in Freund & Schapire 1999 (Machine Learning Large. Margin Classification Using the Perceptron Algorithm).

The quantification method 1 according to the invention allows to obtain a balance quantification in the form of a score or a value between zero and one hundred, proportional to the quality of the balance. For example, a value of less than thirty indicates a poor balance.

In this context, the method may include taking into consideration the quantifier values obtained, the portion rankings or portion scores from several statokinesigrams for the determination of the representative balance value. When the statokinesigrams 110 were generated in a Romberg test, an "eyes open" statokinesigram and an "eyes closed" statokinesigram were obtained. The scores obtained from each of the portions of the "eyes open" and "eyes closed" statokinesigrams are advantageously taken into account in order to obtain a value representative of the balance of the individual.

Preferably, the determination step 50 is followed by a step of recording 60 the balance representative value obtained and possibly associating said value with a unique identifier linked to said individual.

Thus, this allows the individual to compare his/her representative balance value over time. Thus, preferably, the quantification method 1 according to the invention can be implemented for a same individual at different dates in order to monitor the evolution of his/her balance representative value and therefore of the quality of his/her balance.

In addition, advantageously, the method according to the invention may include a step of generating instruction 70 for a graphic representation of the scores of each of the statokinesigram portions 120. Preferably, at least one graph is automatically generated at the end of the step of determining 50 said balance representative value. The balance quantification method 1 according to the invention may also comprise a step of graphically representing said balance representative value. The value can be subject to a display via a display module. This display can be a simple display indicating a value or a graphical representation. The method may also include a step of graphically representing, on a viewing means 270, the value of at least one quantifier 140, a score or a category for each of the statokinesigram portions 120 generated in the segmentation step 20 as a function of time. FIG. 3 shows an example of a graph that can be generated during the implementation of the method according to the invention. The graph in FIG. 3 includes sixteen portions, the color of which depends on the score of each of the portions. The score may be representative of the regularity or irregularity of the displacement of the center of pressure in this portion. The study of FIG. 3 shows that the displacement of the center of pressure becomes increasingly irregular while the displacement was rather regular at the beginning of acquisition.

The method according to the invention may also allow the graphical representation of the evolution of the balance representative value over time or the placement of this value within a group of individuals.

Said balance representative value can also be transmitted to remote systems such as tablets, servers, or personal computers. Thus, the quantification method 1 according to the invention may comprise a step of transmitting the balance representative value, the calculated quantifiers and/or the calculated parameters to at least one communicating system such as a tablet, a server, or a computer, via at least one communication network.

Preferably, the invention relates to a balance quantification method 1 comprising quantifying the static balance and the dynamic balance. Even more preferably, the invention relates to the quantification of the static balance.

As part of the development of this new balance quantification method 1, the inventors verified the relevance of the balance representative value obtained via the statistical models developed and especially the scoring algorithms used via ROC curves. The statistical models developed and especially the scoring algorithms 500 used by the inventors allow to obtain AUCs greater than 0.75.

According to one aspect, the invention relates to a balance quantification device 2 able to implement the balance quantification method 1 according to the invention. More particularly, the balance quantification device 2 according to the invention includes:

a communication module 210, able to receive data comprising at least one statokinesiogram 110 of said individual, a storage means 280, able to record the statokinesigram 110, and a data processing module 220.

A balance quantification device 2 according to the invention is shown schematically in FIG. 5.

The communication module 210 is configured to receive and transmit information to remote systems such as platforms, tablets, telephones, computers, or servers. The communication module allows to transmit the data on at least one communication network and may comprise a wired or wireless communication. Preferably, the communication is operated via a wireless protocol such as wifi, 3G, 4G, and/or Bluetooth.

The communication module 210, for example, allows to receive and transmit information to remote systems such as tablets, telephones, computers, or servers. This information can be raw data of the displacement of the center of pressure or of the statokinesigrams 110. It is also configured to send the data related to the portions, the calculated parameters, the calculated quantifiers, and the balance representative value. These data exchanges may take the form of sending and receiving files containing the raw values of the pressure sensors, files containing the coordinates of the trajectory of the center of pressure, and files including the portions 120, the trajectory parameters 130, the quantifiers 140, and the balance representative values determined from statokinesigram portions 120. The exchanged data can preferably be transferred in an encrypted form and associated with a key specific to the individual being studied. The communication module 210 is also capable of enabling communication between the device 2 and a remote terminal, including a client 400. The customer is generally any hardware and/or software likely to access the quantification device according to the invention.

The data processing module 220 is configured to:
Segment, as a function of time, the statokinesigram 110 of an individual, transmitted by the communication module 210, so as to generate several statokinesigram portions 120,
Extract, from the statokinesigram portions 120, values of at least one trajectory parameter 130,
Determine several quantifiers 140, from the extracted values of the trajectory parameters 130,
Determine a value representative of the balance of the individual from the values of said quantifiers 140 of each of the statokinesigram portions 120.

Preferably, the data processing module 220 is configured to implement the different steps of the quantification method 1 according to the invention. Thus, the preferred steps of the balance quantification method 1 according to the invention are also preferred configurations for the data processing module 220 according to the invention.

Advantageously, the data processing module 220 has a processor and is able to connect to a storage means 280.

The storage means 280 may comprise a transient memory and/or a non-transient memory. It is able to record, for example in the form of files, the raw values of the pressure sensors, the coordinates of the trajectory of the center of pressure, the portions 120, the trajectory parameters 130, the quantifiers 140, and the balance representative values determined from the statokinesigram portions 120. The non-transient memory allows, for example, the configuration of the data processing module to be recorded, while the non-transient memory allows, for example, the statokinesigram 110 to be recorded. The non-transient memory can be a medium such as a CD-rom, a memory card, or a hard drive hosted on a remote server.

The quantification device 2 according to the invention may also include a module 230 for generating a statokinesigram 110. This module is configured to generate the data related to a statokinesigram 110 (for example position along the x- and y-axes as a function of time) from raw data of the displacement of the center of pressure such as generated by force or pressure sensors.

The quantification device 2 according to the invention may also include a re-sampling module 240. Indeed, not all devices able to generate raw data of the displacement of the center of pressure or statokinesigrams 110 provide a controlled sampling frequency. Thus, some devices may lead to a statokinesigram 110 being generated with a first random frequency, the frequency of which cannot be predicted because it constantly varies during the acquisition, for example, for a same statokinesigram 110, between 10 and 1000 Hz. However, such a frequency variation can lead to decreases in the performance of the balance quantification method 1 according to the invention. Thus, preferably, the re-sampling module is configured to process the raw data or the statokinesigrams 110 at a first frequency in order to generate statokinesigrams 110 re-sampled at a second frequency and having a substantially constant frequency. By substantially constant frequency, is to be understood a frequency varying by less than 10% within the statokinesigram 110, preferably varying by less than 5%, even more preferably by less than 1%. The statokinesigram 110 at a second frequency, generated by the re-sampling module 240, has a sampling frequency equal to at least 25 Hz. Preferably, the second frequency is substantially identical to the frequency of the reference statokinesigrams 111.

The balance quantification device according to the invention may comprise a denoising module configured to filter the raw data generated by the pressure or force sensors in order to reduce or suppress interference signals. Denoising can be based on various methods such as wavelet denoising, thresholding, Wiener filter, and deconvolution.

The device may also comprise a control interface. This control interface is configured to allow a user to interact with the balance quantification device. It may comprise, for example, manual actuators (for example buttons) or a touch screen able to receive user commands.

The device may also comprise a display module or viewing means 270. This display module may comprise a liquid crystal display. It allows to display various information such as the results of the quantification, the balance representative value, the progression over time of said value and its positioning in relation to the balance representative values within a group of people.

As just presented, the acquisition device 1 according to the invention comprises a plurality of modules. These modules are separate in FIG. 5, but the invention may provide for different types of arrangements, such as a single module combining all the functions described here. Similarly, these modules can be divided into several electronic boards or gathered on a single electronic board. Similarly, when an action is given to a device or module, it is actually performed by a microprocessor in the device or module controlled by instruction codes stored in a memory. If an action is given to an application, it is actually performed by a microprocessor in the device, in a memory of which the instruction codes corresponding to the application are stored. When a device or module sends or receives a message, this message is sent or received by a communication interface. The memories referred to in this invention may correspond to a random access memory and/or a mass memory. The mass memory can be a medium such as a CD-rom, a memory card, or a hard drive hosted on a remote server.

According to another aspect, the invention relates to a balance quantification system 3 shown in FIG. 6, adapted to implement the quantification method 1 according to the invention. Preferably, the system 3 for quantifying the balance of an individual comprises:

- a platform 310, said platform 310 being adapted to receive an individual and comprising pressure and/or force sensors 312 configured to generate raw data 313, at a first frequency, as a function of a pressure exerted by the feet of the individual on the platform 310,
- a raw data processing unit 320, arranged to obtain at least one statokinesigram 110 of the individual from the raw data 313 generated by the platform 310, and
- a balance quantification device 2, described previously, able to communicate with the processing unit 320.

As shown in FIG. 6, the platform 310 according to the invention is a support intended to receive an individual and able to measure the displacement of a center of pressure using force and/or pressure sensors. Any sensor system for measuring the center of pressure can be used. The only requirement is that the platform 310 must be able to produce raw data for positioning the center of pressure. This support can for example be a pair of soles or at least a tray. Preferably, the platform 310 includes a tray 311. As a general rule, the dimensions on one side of the tray 311 may be between 15 and 70 cm, preferably in the order of 25 to 40 cm. This tray 311 can, for example, include a template allowing a reproducible positioning of the feet, between individuals and over time for a same individual.

The platform 310 is configured to measure the pressure or forces applied onto the tray at a given time and includes sensors 312 to that end. The sensors will transform the applied force into an electrical, optical, or magnetic signal corresponding to the raw data. These raw data can be combined and processed so as to specify the coordinates of the center of pressures and to monitor its variations over time. These sensors can be pressure or force sensors. A force sensor measures the resultant of the support forces of a standing subject. The measurement of the forces and moments exerted at the platform allows to specify the coordinates of the center of pressure and to monitor its variations over time. A pressure sensor may comprise, for example, a pressure cell configured to measure or detect the pressure induced by the weight of the individual placed on the tray or the pressure exerted by the feet of the individual on the platform. The data derived from these sensors are the raw data. The platform 310 can also comprise a plurality of resistive or piezoelectric sensors (for example between 1,000 and 6,000 sensors). There are preferably 4 sensors, located at the ends of the platform, for example 20 to 50 cm apart for the right and left or top and bottom sensors. For example, as shown in FIG. 6, the platform 310 has four sensors 312 located at the four corners of the tray (Top left, Top right, Bottom left, Bottom right).

The platform 310 advantageously includes a time counting module and can be configured to measure the values of its various sensors 312 at a random interval, at a frequency that can vary, for example, from 10 Hz to 1,000 Hz. Preferably, the platform 310 is configured to measure the values of its various sensors 312 at a frequency greater than or equal to 25 Hz, more preferably greater than or equal to 50 Hz.

Even more preferably, the platform 310 is configured to measure, when acquiring a statokinesigram 110, the values of its various sensors 312 at a frequency greater than or equal to 25 Hz and in a substantially constant manner. Indeed, if the sampling frequency is too low, or too random, the quantification of the balance will not be sufficiently accurate. If the frequency is not constant, then preferably the average acquisition frequency is greater than or equal to 60 Hz, more preferably greater than or equal to 75 Hz.

The platform 310 may include a display device, preferably positioned so that the individual, standing on the tray 311, can see the display device.

The platform 310 may also include a speaker device that can give instructions to the individual (for example getting on or off the tray 311). These instructions can also be given by the display device.

Advantageously, it is possible to increase the sensitivity of the quantification by using a foam placed on the platform and able to deform or disturb the proprioceptive and tactile information. This foam can, for example, have a thickness of 1 to 10 millimeters and a density between 100 and 500 $kg/m^3$.

The platform 310 can also include a module for measuring the weight of the individual, his/her fat, water, bone, muscle mass, his/her heart rate, and/or his/her body mass index.

The balance quantification system 3 also includes a unit for processing the raw data 320 generated by the platform. This raw data processing unit 320 is arranged and/or configured to generate at least one statokinesigram 110 of the individual, from the raw data generated by the sensors 312. This raw data processing unit 320 can be integrated, for example, into the platform 310 as shown in FIG. 6. However, it can also be integrated into a remote server 330, into the quantification device 2 (for example it then also integrates the module 230 for generating a statokinesigram 110) or into a control device 340.

The balance quantification system 3 may include a remote server 330 as shown in FIG. 6. For example, it is possible to access this remote server 330 via a web interface or directly via the appropriate functions implemented directly on a control device 340. All communications between the control device(s) 340 and the remote server 330 can be secured, for example by HTTPS protocols and AES 512 encryption.

This remote server can host the quantification device 2. Thus, a single quantification device 2 can monitor a plurality of individuals.

The quantification system according to the invention may include a system control device 340 configured to interact with the platform 310 and the balance quantification device 2. This system control device 340 allows, for example, to control the data acquisition from the platform 310 and to display the results from the quantification device 2.

This system control device 340 is preferably a mobile device such as a tablet 340a, a laptop, or a watch.

According to another aspect, the invention relates to a computer program product 4 configured to implement the balance quantification method 1 according to the invention. The computer program product 4 is recorded on a non-transient memory medium and can run on a computer, a tablet, or a server; said computer program including at least:

- one algorithm adapted to segment a statokinesigram 110 of an individual so as to generate several statokinesigram portions,
- one algorithm adapted to extract, from the statokinesigram portions 120, values of at least one trajectory parameter 130,
- one algorithm adapted to determine several quantifiers 140, from the extracted values of the trajectory parameter 130, and one algorithm adapted to determine a value representative of the balance of the individual from the values of said quantifiers 140 each of the statokinesigram portions 120.

The method, device, system, and computer program product according to the invention allow for the quantification of the balance of an individual and can have many applications. Indeed, the invention allows to provide a measuring tool, namely a method, the device for implementing the method, and the system integrating the device, which allows a numerical and objective value of the balance of an individual to be obtained in order to answer several main questions relating to the balance of an individual such as the evolution of the balance, whether natural or under treatment, the quality of the balance and therefore, its corollary, the severity of a possible balance disturbance (for example what is the risk of falling?), and the cause or causes of the possible balance disturbance.

Indeed, generating a value representative of the balance of an individual and indicative of the quality of his/her balance allows the individual, or others, to assign a numerical and objective value to this balance.

These values or scores can be used as part of a monitoring over time to identify deviations from the learned reference.

Similarly, the invention can be used to highlight the effects of different treatments and the recovery rate could be monitored by the quantification of the balance according to the invention. Thus, the invention can be implemented in the context of performance evaluation of sports programs, prostheses, sports shoes, compensation insoles, rehabilitation protocols, neurological disorder treatment and/or surgical techniques. The method according to the invention is particularly adapted to the elderly.

In addition, the invention can be used to compare the quality of the balance of an individual with the quality of the balance of other individuals and determine, for example, whether the individual is at risk of falling. Thus, the invention can be implemented as part of the measurement of a risk of falling, for example, at 6 months. In this context, the balance representative value determined by the quantification method 1 according to the invention, an indicative value of a risk of falling at 6 months. In particular, the individual, within the meaning of the invention, is a person over 60, preferably over 70.

In addition, comparing the values of the quantifiers 140 obtained in an individual with values of the quantifiers obtained in different categories of people can help to target how the individuals should be cared for and to direct them to appropriate services (for example traumatology, rheumatology, neurology). Thus, the invention can be implemented in the context of determining the origin of the balance disorder.

Examples

Individuals Studied

The results shown below were obtained according to a protocol approved by the Agence National de Sécurité du Médicament et des produits de santé and written consent was obtained for all participants. The invention was implemented on a group of 126 individuals with the following characteristics:

- over the age of 65,
- in good health (for example patients with hypertension were excluded)
- able to stand on the platform,
- having given informed consent.

Of the 126 individuals included in the study, 18 reported a fall in the 6 months prior to the consultation.

Measurement of the Displacement of the Center of Pressure

During the consultation, the movements of the center of pressure of the individuals were monitored using a Wii Balance Board (registered trademark) and recorded using a custom application specially developed as part of the invention. The feet were positioned in the most comfortable position for the patient, without exceeding the width of the shoulders. The trajectory of the center of pressure was recorded for 25 seconds with the eyes open, and then for 25 seconds with the eyes closed. A fall questionnaire was completed for each individual in order to record reported falls that occurred in the last 6 months.

Pre-Processing

Before calculating the statokinesigrams, the output of the raw signals by the WBB was denoised and re-sampled.

Segmentation

The statokinesigrams were then segmented into 1 to 3 second portions with or without overlap.

Statistical Analysis According to the Invention

For each portion of the statokinesigram, three quantifiers were calculated: the area of the 95% confidence ellipse, the mean of the norm of the rate of displacement of the center of pressure, the variance of the values of the position of the center of pressure along the medial-lateral axis. These quantifiers were then normalized.

Two Gaussian Mixture Models (GMM) were used, one for the eyes open, the second for the eyes closed. Gaussian Mixture Models (GMM) are unsupervised partitioning algorithms.

Considering a number of category k (in this example, k=2 for a regular-RP or irregular-IP displacement of the center of pressure), and a set of points Zj (here each point Zj corresponds to the normalized quantifier values for each of the portions), the GMM tries to construct a mixture of 2 (k) multivariate random Gaussian variables, according to the principle of maximum likelihood. To do so, it proceeds with the principle of the expectation-maximization (EM) algorithm in order to maximize the likelihood law in the presence of incomplete data by iteratively maximizing the log-likelihood expectation.

The weights $\pi_i$, the centers $(\mu_i)^k_{i=1}$ and the covariance matrix of each Gaussian random variable $N_i$ are initialized randomly using the classical iterative procedure (for example 20 times). Then, the algorithm repeats the following steps until convergence.

The probability $p_{i,j}$ that the point $Z_j$ belongs to the group i:

$$p_{i,j} = \frac{\frac{\pi_i}{\sqrt{|\Sigma_i|}} \exp\left(-(Z_j - \mu_i)^T \sum_i^{-1} (Z_j - \mu_i)\right)}{\sum_i \frac{\pi_i}{\sqrt{|\Sigma_i|}} \exp\left(-(Z_j - \mu_i)^T \sum_i^{-1} (Z_j - \mu_i)\right)}$$

The weights $\pi_i$, the centers $(\mu_i)^k_{i=1}$ and the covariance matrix are updated according to the probability $p_{i,j}$ $$\pi_i = \frac{1}{n} \sum_j p_{i,j}$$

-continued $$\mu_i = \frac{1}{\sum_j p_{i,j}} \sum_j p_{i,j} Z_j$$

$$\sum_i = \frac{1}{\sum_j p_{i,j}} \sum_j p_{i,j} (Z_j - \mu_i)^T (Z_j - \mu_i)$$

This allows a score to be calculated from the results obtained for each portion.

Comparative Statistical Analysis, Wavelet

In the literature, it is mentioned that in the context of a wavelet analysis, each frequency band can be linked to different sensory inputs. For example, the study of energy distribution could allow different balances to be differentiated. Thus, three frequency bands were studied on this sample in order to analyze the distribution of energy in these bands. As in the analysis proposed according to the invention, the final performance is verified by averaging the scores of each portion and creating an overall score. The final score in the wavelet analysis is the percentage of energy contained in these bands. Such an analysis allows an AUC result between 0.48 and 0.52 to be obtained, which is a random result.

Thus, the wavelet method does not seem to be adapted to the problems addressed by the present invention.

RESULTS OF THE INVENTION

The results of AUC as a function of the parameters applied to the method and in comparison with an analysis performed without segmentation are shown in Table 1 below.

These results show that with the selected quantifiers and in the absence of segmentation, the AUC results are 0.63 with a standard deviation of 0.12.

Conversely, when segmentation is present, the AUC results are at least 0.75, namely a minimum increase of 19%, and the standard deviation is lower for all conditions tested. Thus, the implementation of the method according to the invention allows the performance of the balance quantification to be improved and its variability to be reduced.

In addition, with a 50% overlap, the AUC can be further increased with, for portions of a second, an AUC of 0.77.

TABLE 1

| Duration of each portion | 50% overlap AUC (deviation) | Without overlap AUC (deviation) |
| --- | --- | --- |
| 1 sec | 0.77(0.09) | 0.75(0.11) |
| 2 sec | 0.77(0.10) | 0.75(0.11) |
| 3 sec | 0.76(0.09) | 0.75(0.08) |
| Without segmentation | na | 0.63(0.12) |

Thus, the invention provides a measuring tool for obtaining an improved quantification of the balance of an individual. In particular, this quantification can take into account weak signals, transient imbalances that could be masked during the analysis of complete statokinesigrams. In addition, the invention allows to facilitate the appreciation of the balance of an individual made through graphic representations for qualifying each portion of a statokinesigram. Advantageously, a user will be able to navigate easily through this dataset and will be able to identify, where necessary, characteristic patterns of balance disorders.

All of these advantages contribute to improving the quantification of the balance of an individual.

The invention claimed is:

1. A method for quantifying the balance of an individual to obtain a value representative of the balance of said individual, said method being implemented by a device comprising at least one processor connected to a memory, said method comprising:
   recording, on the memory, at least one statokinesigram of the individual obtained from a platform on which the individual is standing, the platform comprising pressure and/or force sensors, and the statokinesigram comprising data related to a trajectory or displacement of a center of pressure;
   segmenting as a function of time, at least one of the statokinesigrams of the individual recorded on the memory, by the processor, to generate several statokinesigram portions;
   extracting, by the processor and from the statokinesigram portions, values of at least one trajectory parameter, the trajectory parameter being a position, stability, and/or dynamics trajectory parameter of the center of pressure;
   determining, by the processor, values of at least two quantifiers, from the values of trajectory parameters extracted in the extraction step, for each of the statokinesigram portions generated in the segmentation step;
   inputting the determined values of said quantifiers to an unsupervised partitioning algorithm, the unsupervised portioning algorithm being implemented by the processor and being configured to output an assigned score or category classification for each of the statokinesiogram portions; and
   determining, by the processor, said value representative of the balance of the individual based on the assigned scores or category classifications for each of the statokinesiogram portions, as output by the unsupervised partitioning algorithm,
   wherein each of the statokinesigram portions is one second to three seconds long, and
   wherein consecutive statokinesigram portions have an overlap ratio of 25% to 95%.

2. The quantification method according to claim 1, wherein the segmenting step generates, for each statokinesigram, at least ten statokinesigram portions.

3. The quantification method according to claim 1, wherein the unsupervised partitioning algorithm is an unsupervised Gaussian mixture model, a hierarchical bottom-up classification, or a hierarchical top-down classification.

4. The quantification method according to claim 1, further comprising:
   generating raw data corresponding to a displacement of the center of pressure, the pressure being applied by the whole body of the individual over time on the platform.

5. The quantification method according to claim 4, further comprising:
   transforming the raw data into trajectory data of the center of pressure.

6. The quantification method according to claim 4, wherein the raw data corresponding to the displacement of the center of pressure is obtained in a Romberg test.

7. The quantification method according to claim 6, wherein the at least one of the statokinesigrams comprises a statokinesigram obtained while the individual has his/her eyes open (O) and a statokinesigram obtained while the individual has his/her eyes closed (F), and wherein the method further comprises, for at least one of the quantifiers, calculating an O/F or F/O ratio corresponding to a ratio between the value of the trajectory parameter calculated from the statokinesigram obtained while the individual has his/her eyes open (O) and the value of the trajectory parameter calculated from the statokinesigram obtained while the individual has his/her eyes closed (O/F ratio) or the opposite (F/O ratio).

8. The quantification method according to claim 1, wherein the trajectory parameter is a position trajectory parameter, and the position trajectory parameter is:
   a position of the center of pressure along an X-axis, corresponding to the position of the center of pressure compared to a median line of an orthonormal reference frame in a plane of the X-axis;
   a position of the center of pressure along a Y-axis, corresponding to the position of the center of pressure with respect to a median line of an orthonormal reference frame in a plane of the Y-axis; or
   a radius in polar coordinates, corresponding to a distance of the center of pressure from an average position of the center of pressure according to the orthonormal reference plane.

9. The quantification method according to claim 1, wherein the trajectory parameter is a stability trajectory parameter, and the stability trajectory parameter is:
   a radial balance corresponding to a maximum distance of the center of pressure from its current value at a given time over a predefined duration between 0.1 and 2 seconds;
   a time balance corresponding to a time required for the center of pressure to move more than a distance between 1 and 10 millimeters away from its current position at any given time; or
   a ballistic interval corresponding to a time interval between two balance positions.

10. The quantification method according to claim 1, wherein the trajectory parameter is a dynamics trajectory parameter, and the dynamics trajectory parameter is:
    a velocity of the displacement of the center of pressure, calculated for all sampling points of the displacement of the center of pressure over the duration of the acquisition;
    an acceleration of the displacement of the center of pressure, calculated for all sampling points of the displacement of the center of pressure over the duration of the acquisition;
    a power corresponding to a value of a scalar product of a velocity and acceleration calculated for all sampling points; or
    a deviation corresponding to a normal of a vector product of the velocity and acceleration calculated for all sampling points.

11. The quantification method according to claim 1, wherein the quantifiers calculated for each portion of the statokinesigram are a mean value, a variance, a square mean, or an extreme value, of the extracted trajectory parameter.

12. A device for quantifying the balance of an individual, said device comprising:
    a receiver and/or transmitter configured to receive a statokinesigram of said individual obtained from a platform on which the individual is standing, the platform comprising pressure and/or force sensors, and the statokinesigram comprising data related to a trajectory or displacement of a center of pressure;
    a memory configured to record said statokinesigram; and
    at least one processor configured to connect to the memory and configured to:
       segment, as a function of time, the statokinesigrams of the individual recorded on the memory to generate several statokinesigram portions;
       extract, from the statokinesigram portions, values of at least one trajectory parameter, the trajectory parameter being a position, stability, and/or dynamics trajectory parameter of the center of pressure;
       determine several quantifiers from the extracted values of the at least one trajectory parameter;
       input the determined values of said quantifiers to an unsupervised partitioning algorithm, the unsupervised portioning algorithm being implemented by the processor and being configured to output an assigned score or category classification for each of the statokinesiogram portions; and
       determine a value representative of the balance of the individual based on the assigned scores or category classifications for each of the statokinesiogram portions, as output by the unsupervised partitioning algorithm,
    wherein each of the statokinesigram portions is one second to three seconds long, and
    wherein consecutive statokinesigram portions have an overlap ratio of 25% to 95%.

13. The quantifying device according to claim 12, wherein the processor is further configured to process raw data or the statokinesigrams at a first frequency to generate re-sampled statokinesigrams at a second frequency and having a substantially constant frequency.

14. A system for quantifying the balance of an individual, comprising:
    a platform, said platform being configured to receive an individual and comprising pressure and/or force sensors configured to generate raw data, at a first frequency, as a function of a pressure exerted by the feet of the individual on the platform,
    a raw data processor, configured to obtain at least one statokinesigram of the individual from the raw data generated by the platform, and
    the quantifying device according to claim 12, configured to communicate with the raw data processor.

15. The quantification system according to claim 14, wherein the platform includes four pressure and/or force sensors.

16. The quantification system according to claim 14, wherein the platform is configured to measure values of its different pressure and/or force sensors at a frequency greater than or equal to 25 Hz and substantially constantly.

17. The quantification system according to claim 14, wherein the platform includes a foam capable of deforming or disturbing proprioceptive and tactile information.

* * * * *